US009835525B2

(12) United States Patent
Husveg

(10) Patent No.: US 9,835,525 B2
(45) Date of Patent: Dec. 5, 2017

(54) MULTIPHASE SAMPLE CONTAINER AND METHOD

(71) Applicant: TYPHONIX AS, Bryne (NO)

(72) Inventor: Trygve Husveg, Varhaug (NO)

(73) Assignee: Typhonix AS, Bryne (NO)

( * ) Notice: Subject to any disclaimer, the term of this patent is extended or adjusted under 35 U.S.C. 154(b) by 495 days.

(21) Appl. No.: 14/364,926

(22) PCT Filed: Dec. 14, 2012

(86) PCT No.: PCT/NO2012/050249
§ 371 (c)(1),
(2) Date: Jun. 12, 2014

(87) PCT Pub. No.: WO2013/089564
PCT Pub. Date: Jun. 20, 2013

(65) Prior Publication Data
US 2014/0366653 A1 Dec. 18, 2014

(30) Foreign Application Priority Data
Dec. 16, 2011 (NO) .................................. 20111734

(51) Int. Cl.
*G01N 1/20* (2006.01)
*G01N 1/10* (2006.01)
(Continued)

(52) U.S. Cl.
CPC ............ *G01N 1/10* (2013.01); *G01N 33/1833* (2013.01); *G01N 33/2823* (2013.01); *G01N 2001/2071* (2013.01)

(58) Field of Classification Search
CPC ........ G01N 1/10; G01N 1/2273; G01N 1/405; G01N 2001/2223; G01N 1/2035;
(Continued)

(56) References Cited

U.S. PATENT DOCUMENTS 4,359,907 A * 11/1982 Morin, III ............ G01N 1/2035
324/438
4,631,967 A * 12/1986 Welker .................. G01F 15/185
73/861.25
(Continued)

FOREIGN PATENT DOCUMENTS

| NO | 178807 B | 6/1995 |
| WO | WO 95/18366 | 7/1995 |
| WO | WO 2013/089564 | 6/2013 |

OTHER PUBLICATIONS

Frankiewicz, Ted, et al.; "Diagnosing and Resolving Chemical and Mechanical Problems with Produced Water Treating Systems"; 12th Annual International Petroleum Environmental Conference (IPEC); Nov. 2005; 10 pages.

(Continued)

*Primary Examiner* — John Fitzgerald
*Assistant Examiner* — Truong D Phan
(74) *Attorney, Agent, or Firm* — Winstead PC

(57) ABSTRACT

The invention provides a sample container arrangement for collecting multiphase samples of gas and liquid, particularly oil in water samples that are representative with respect to oil concentration, oil droplet size and oil droplet size distribution, the sample container arrangement comprises a sample container with an upper end, a lower end and a container volume for sample collection, such as a standing cylinder, distinctive in that the container arrangement further comprises: one inlet connected to the upper end or part of the container volume, one outlet with a valve with bleeding function, connected to the upper end or part of the container volume, and one outlet connected to the lower end of the container volume.

12 Claims, 2 Drawing Sheets

Figure 1:
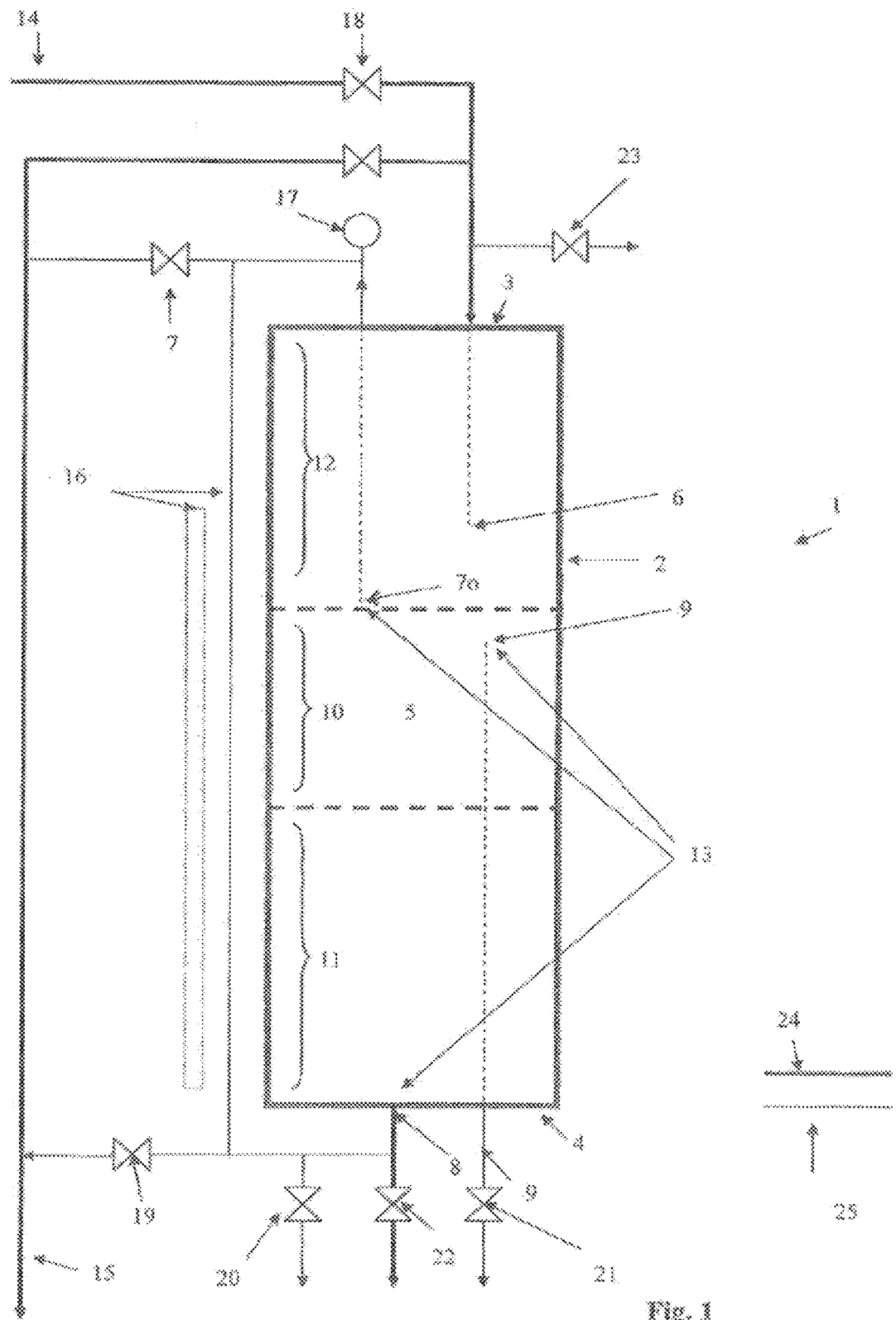

(51) Int. Cl.
*G01N 33/18* (2006.01)
*G01N 33/28* (2006.01)

(58) Field of Classification Search
CPC .......... G01N 30/20; G01N 2001/2071; G01N 33/18; G01N 11/00; G01N 33/4905; G01N 33/2823; G01N 29/024; G01N 33/2847; G01N 27/223; G01N 30/32; G01N 30/34; G01N 30/36; G01N 33/0006; G01F 1/74
USPC ....... 73/863.21, 863.71, 53.01, 61.41, 61.43, 73/61.44, 61.59, 61.56
See application file for complete search history.

(56) References Cited

U.S. PATENT DOCUMENTS

| | | | |
|---|---|---|---|
| 4,844,817 A | 7/1989 | Flanigan et al. | |
| 4,905,510 A | 3/1990 | Brickhouse | |
| 5,033,288 A * | 7/1991 | Castel | G01N 33/2823 73/61.44 |
| 5,253,514 A * | 10/1993 | Kaakinen | B01D 61/12 73/61.73 |
| 6,128,962 A * | 10/2000 | Marrelli | G01F 1/74 324/638 |
| 6,182,505 B1 * | 2/2001 | Segeral | G01N 1/2035 422/68.1 |
| 6,279,385 B1 * | 8/2001 | Krawetz | G01N 11/08 73/53.01 |
| 6,679,280 B1 * | 1/2004 | Pinto | H01M 8/04186 137/14 |
| 7,024,951 B2 | 4/2006 | Germond et al. | |
| 2003/0051565 A1 * | 3/2003 | Nimberger | G01N 1/2258 73/864.34 |
| 2004/0112150 A1 | 6/2004 | Germond et al. | |
| 2007/0256736 A1 * | 11/2007 | Tonkovich | B01F 3/0807 137/92 |
| 2009/0139345 A1 * | 6/2009 | Xie | G01F 15/02 73/861.04 |
| 2010/0145634 A1 * | 6/2010 | Pinguet | G01F 1/46 702/45 |

OTHER PUBLICATIONS

Norwegian Search Report issued in priority Application No. 20111734 dated Jul. 12, 2012, 2 pages.
International Preliminary Report on Patentability issued in priority Application No. PCT/NO2012/050249 dated Nov. 13, 2013, 3 pages.
International Search Report issued in priority Application No. PCT/NO2012/050249 dated Mar. 25, 2013, 3 pages.
Written Opinion of the International Searching Authority issued in priority Application No. PCT/NO2012/050249 dated Mar. 25, 2013, 4 pages.
PCT/NO2012/050249 International Search Report dated Mar. 25, 2013, 3 pages.
PCT/NO2012/050249 International Preliminary Report on Patentability dated Nov. 13, 2013, 3 pages.
NO 20111734 Norwegian Search Report dated Dec. 7, 2012, 2 pages.
Frankiewicz, T., et al., "Compact Induced Gas Flotation as an Effective Water Treatment Technology on Deep Water Platforms", 2005 Offshore Technology Conference, May 2-5, 2005, 6 pages.

* cited by examiner

MULTIPHASE SAMPLE CONTAINER AND METHOD

CROSS-REFERENCE

This application is the National Phase entry of International Application No. PCT/US2012/050249, filed Dec. 14, 2012, which claims priority to Norwegian Patent Application No. 20111734 filed Dec. 16, 2011, both of which are herein incorporated by reference in their entireties.

FIELD OF THE INVENTION

The present invention relates to sampling of multiphase fluid mixtures. More specifically, the invention relates to sample containers and methods for collecting multiphase petroleum samples of gas and liquids, such as gas, oil and water.

BACKGROUND OF THE INVENTION AND PRIOR ART

Sample containers, often called sample bottles or samplers, for collection of samples of petroleum fluids as well as other fluids, are well known in the art. A typical objective is to sample representative samples of a process fluid at a specific processing stage. In order to achieve the objective, it is crucial that the fluid pressure is maintained during the sampling procedure. Other parameters known in the art are constant temperature and no mixing with non-representative fluid, such as fluid left in dead volumes in the sample bottle or its connections.

A typical sample bottle design is to have a divided chamber with a movable piston between the chambers. One part of the chamber contains a pressurized back pressure fluid, for which the pressure typically equals the pressure of the process fluid to be sampled. The other part of the divided chamber is the sample chamber, into which the sample is brought without fluctuating the pressure too much. Thereby pressure induced phase transformations of the fluid phases are reduced or avoided.

Another type of sample containers has a single sample volume, and such sample containers are typically connected as a parallel flow of a process stream. Flowing a fraction of the process flow through the sample container for a while, provides, at least in theory, a representative sample that can be isolated from the stream without fluctuating the pressure too much.

However, free gas flotation during container filling and dissolved gas flotation during container filling or pressure release often cause severe problems, particularly for (oil in) water and (water in) oil sample collection and analysis. Said flotation problems are caused by inappropriate sample bottle designs and methods of operation or both, which will be further explained below. The flotation problem is relevant for being able to sample more realistic samples in order to optimize process and equipment operation, such as the separation process of cleaning produced water down to very low oil contents (currently 30 ppm) allowable for discharge to sea. Other typical problems are related to the length or morphology of the inlet tubing which often affect the fluid qualities by causing shear forces and pressure drop to the flowing fluids. Currently, portable sampling solutions often have a limited ability of collecting samples at high gas/liquid fractions. Furthermore, liquid volumes are typically small for portable sample devices, which sometimes is a disadvantage for subsequent sample analysis since dynamic fluctuations and intermediate process abnormalities have larger effect for small volumes.

Transport regulations may pose a limitation on transport of sample bottles. A typical procedure is depressurization to below bubble point before transport to a laboratory, after which the sample is recombined/recovered in the laboratory for analysis.

Two relevant prior art sample containers are described and illustrated in the patent publications U.S. Pat. No. 7,024,951 and U.S. Pat. No. 6,182,505, however the sample container of U.S. Pat. No. 7,024,851 has a flotation problem and the teaching of U.S. Pat. No. 6,182,505 merely relates to finding volume fractions of phases. Some description of the underlying problem of the present invention can be found in patent publication U.S. Pat. No. 4,844,817, from column 6, and in the paper "Diagnosing and Resolving Chemical and Mechanical Problems with Produced Water Treating Systems" by Frankiewicz, et al. 12th Annual International Petroleum Environmental Conference (IPEC); November 2005.

A demand exists for improved sample containers and methods for sample collection, particularly for collecting oil-in-water and water-in-oil samples not affected significantly by gas flotation effects. The objective of the invention is to meet the demand.

SUMMARY OF THE INVENTION

The invention meets the objective as it provides a sample container arrangement for collecting multiphase samples of gas and liquid, particularly oil in water samples that are representative with respect to oil concentration, oil droplet size and oil droplet size distribution, the sample container arrangement comprises a sample container with an upper end, a lower end and a container volume for sample collection, such as a standing cylinder, distinctive in that the container arrangement further comprises:
  one inlet connected to the upper end or part of the container volume,
  one outlet with a valve with bleeding function, connected to the upper end or part of the container volume, and
  one outlet connected to the lower end of the container volume.

The inlet is arranged to exit in substance above the level of pressurized liquid in the volume, preferably entirely above the pressurized liquid. Preferably the inlet exits at elevation above or equal to the maximum liquid level for pressurized sample collection, most preferably above the liquid level for pressurized sample collection, thereby ensuring that gas introduced through the inlet never will bubble or float up through the pressurized sample liquid. The outlet is arranged in substance in the bottom, preferable at the lowest point of the volume. With the sample container arrangement of the invention, as well as the method of the invention, the problems of flotation affecting the samples and non-representative liquid mixing with the sample, are avoided or greatly reduced, which will be explained and better understood from the description below. For the sake of simplicity, the sample container arrangement is often termed the sample container, or only container. The sample container is preferably an elongated standing container, such as a standing cylinder or pipe section, for facilitating a separation effect in the container volume. However, the sample container can have other orientations or shapes, such as an inclined, laying or horizontal container or pipe section, but the volume must allow a significant separation effect of the collected pressurized sample and with respect to the separation effect of gravity and the direction of gravity, allow separation of the pressurized fluid into a gas volume in an upper end and liquid phases below, such as an intermediate volume of oil and a volume of water in a lower end.

Preferably all of the inlet flow enter the volume above the liquid level for pressurized sample collection, one of the outlets is connected with exit opening at the very bottom level of the container and one further outlet is connected to a higher elevation level of the volume, the outlet levels in the volume correspond to different pressurized liquid phase parts of the volume.

The inlet exit above the liquid level and ensures that the isobaric collected pressurised liquid is not affected by flotation by dispersed gas bubbling up the liquid or dissolved gas release causing flotation. Preferably the inlet is a vertical pipe closed in a lower end but with openings for radial inlet flow into the gas volume above the liquid, an alternative is a so called china hat design. Standard design according to prior art is to have the inlet at the container bottom, which results in flotation by all of the gas of the sampled fluid, the flotation removes oil from the water phase as described in OTC 17612. Having one of the outlet exits at the bottom level of the container, all liquid collected during the initial container pressurization can be emptied before the actual isobaric sample filling takes place, so as not to affect, change or disturb the measurements. During the initial pressurization the sample container pressure increases from typical atmospheric pressure to the process sampling point, stage or pipeline pressure, which pressure can be hundreds of bars, the collected liquid is affected by this pressure change and is therefore not representative. During initial pressurization, the collected fluid is subject to pressure decrease whilst the container is subject to pressure increase.

Preferably, the outlet to the valve with bleeding function in top of the container is at about maximum liquid filling level of pressurized fluid. The oil and water ratios of the liquid filled in the container will correspond to the oil-water ratio of process liquid in the container inlet. A liquid level indicator, a liquid sensor means in the tubing, a liquid level sensor in the container or any other liquid level means, such as a window in the container, is preferably arranged to measure liquid level filling. However, the exact filling level of pressurized liquid is not critical as long a significant pressurized gas volume is present in the top part of the container volume, allowing small samples of pressurised liquid to be collected without affecting the container pressure level significantly.

The outlets for sample collection can be arranged in many ways. Preferably, outlets are arranged from the container ends with internal tubing having inlet or opening at different elevation levels, the levels correspond to oil, water and optionally gas phase parts of the volume. The different outlets are fluidly connected to different phases in the container volume. Outlets are alternatively or in addition arranged from the side of the container at different elevation levels. In other words, the opening of the internal outlet tubing or outlets are at specific elevation levels corresponding to container volume parts corresponding to specific phases, usually water, oil and gas. Thereby pressurized phase samples, unaffected by flotation, mixing, shear and pressure changes, can be collected.

The sample container of the invention may comprise one or several of numerous preferable features, such as a liquid level indicator, a manometer arranged in the line to a needle valve with bleeding function or another place, flowmeters in the inlet and outlets, a thermometer, ball valves for open/close function arranged in inlet and outlet tubing, needle valves arranged in outlet tubing and also arranged to the inlet line for gas sampling and as the valve with bleeding function and in a line connecting the container outlet to a pipeline or process stage and other features the person skilled in the art may contemplate as favourable. Preferably the container arrangement comprises a logger, such as a pressure, temperature and time logger or a pressure, flow rate and time logger, or a logger for any selected group of parameters, in order to document the sample history.

Preferably, the diameter of pressurized sample taking outlet tubes and pressure bleeding or pressure control tubes are smaller than the diameter of the inlet tube. This has effect by securing a reduced shear action on the fluid that is filled, the shear action induces changes to the fluid, which changes are thereby reduced.

The invention also provides a method for collecting multiphase samples of gas and liquid, particularly oil in water samples that are representative with respect to oil concentration, oil droplet size and oil droplet size distribution, using a sample container such as a standing cylinder comprising an upper end, a lower end, a container volume for sample collection, one inlet and one outlet with a valve with bleeding function connected to the upper end or part of the container volume and at least one outlet connected to the lower end of the container volume. The method is distinctive by the steps:

to open an inlet valve, with other valves connected to the container in closed position, in order to pressurize the container to a process pressure,
   to empty the container volume isobaric for liquid that has been collected during the pressurization, by bleeding out liquid from the bottom of the volume,
   when the pressurized container is emptied for liquid, to close the liquid emptying valve connected to the bottom of the volume, to open the valve with bleeding function connected to the top of the volume and then fill up the container isobaric with liquid up to a prescribed liquid filling level, maintaining a gas volume in top of the volume, after which the inlet preferably is closed, and
   to take a pressurized liquid sample from the lower end outlet and optional further fluid samples, also from further optional outlets at different elevation levels in the container volume.

The method preferably comprises the further steps:
   to take pressurized phase samples from sample outlets corresponding to elevation levels for the respective fluid phases, such as water in oil and oil in water samples that are unaffected by flotation and thereby representative with respect to concentration of the dispersed phase, and optionally gas phase samples,
   to depressurize the container by bleeding out the pressure, and
   to take fluid phase samples of depressurised fluid for both concentration and droplet size/droplet size distribution analysis.

Further preferable or more detailed steps comprise:
a) the pressurised samples are subject to oil-in-water concentration and water-in-oil concentration measurements,
b) the depressurised samples are subject to oil-in-water concentration and water-in-oil concentration measurements, c) oil-in-water and water-in-oil droplet size analysis are undertaken on depressurized/affected samples of oil and water, respectively, optionally also on unaffected/pressurized samples, and d) the relative difference between a) and b) are used to qualify c) or alternatively, to quantify/estimate the real values of c).

The invention also provides use of the sample container arrangement of the invention, for collecting oil-in-water and water-in-oil samples for analysis of the concentration of the dispersed phase, particularly with pressurised samples not affected significantly by flotation effects.

FIGURE

The invention is illustrated with two figures, namely

Figure 2:
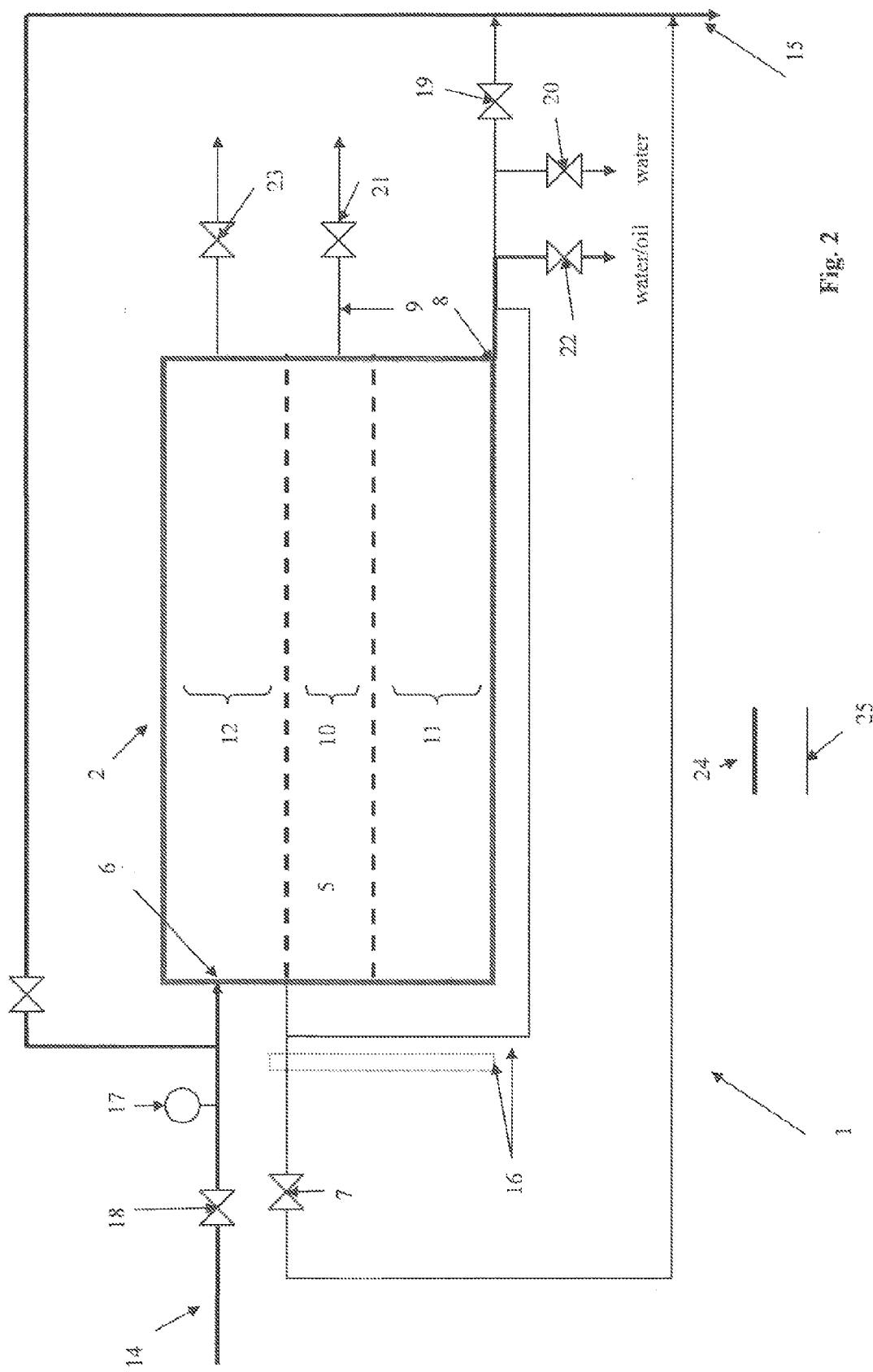

FIG. 1 illustrating an embodiment of a sample container arrangement of the invention, and FIG. 2 illustrating an alternative embodiment of a sample container arrangement of the invention.

DETAILED DESCRIPTION

Reference is made to FIG. 1 illustrating one of many possible embodiments of a sample container arrangement 1 of the invention for collecting multiphase samples of gas and liquid, particularly water samples that are representative with respect to concentration of oil, and oil droplet size distribution, and oil samples that are representative with respect to concentration of water and water droplet size distribution. The sample container arrangement comprises a standing sample container 2 with an upper end 3, a lower end 4 and a container volume 5 for sample collection, one inlet 6 connected to the upper end 3 of the container volume, one valve 7 with bleeding function, such as a needle valve, connected to the upper end 3 of the container volume, and one outlet 8 connected to the lower end of the container volume. The illustrated sample container is a standing cylinder. The inlet 6 exits above the liquid level for pressurized sample collection, ensuring that no pressurized liquid is subject to flotation. A further outlet 9 is fluidly connected to a oil elevation level of the volume, that is an oil phase part 10 of the volume, and the bottom outlets are from a water phase part 11 of the volume. The valve 7 with bleeding function is connected to an outlet 7o with opening or inlet that in the illustrated embodiment correspond to the maximum filling level of pressurized liquid, above which level the volume contains pressurized gas 12. The pressurized gas will in substance maintain the container pressure even though samples are taken, allowing the sample collection to be isobaric, which in this context means at the same pressure, exact or in substance so that the dispersed phase concentration of the samples are not or only very little affected. Several outlets 13 are at different elevations. The sample container is connected to a process sampling point, not shown, with a barrier valve, not shown, with an inlet hose or pipe 14. An outlet pipe or hose 15 is connected to a discharge point, preferably of atmospheric pressure or a low pressure corresponding to a specific low pressure point or stage of a process. The illustrated sample container further comprises a liquid level indicator 16, a manometer 17, an inlet valve 18, a liquid flushing valve 19, a water sampling valve 20, an oil sampling valve 21, a water and oil outlet valve 22 feasible for taking depressurised samples of water and oil, and a gas sampling valve 23. Different pipe, tubing or hose diameters are illustrated with different line thicknesses, more specifically ½" tubing is illustrated with thicker line 24 whilst ¼" tubing is illustrated with thinner line.

A typical sample procedure, using the illustrated sample container arrangement embodiment, can be as follows:

I to open the inlet valve 18, with other valves connected to the container in closed position, in order to pressurize the container to a process pressure. This is verified with the manometer.

II to empty the container volume isobaric for liquid that has been collected during the pressurization, by bleeding out liquid from the bottom of the volume, by opening liquid flushing valve 19. Pressure and preferably also temperature is kept equal to the process inlet pressure and temperature over a period of time whilst flushing, verified by the manometer and optional thermometer.

III when the pressurized container is emptied for liquid, which can be verified by the level indicator, to close the liquid emptying or flushing valve 19 connected to the bottom of the volume, to open the valve 7 with bleeding function connected to the top of the volume and then fill up the container isobaric with liquid up to a prescribed liquid filling level 26, maintaining a gas volume in top of the volume, after which the inlet valve is closed. Pressure is still kept equal to the process pressure, the sample fluid is given time to separate, which typically require 4-5 minutes. By filling through the top, the sampled liquid has not been subject to flotation by dispersed gas during filling, eliminating a major source of error. High gas liquid ratio is not causing any problem for the sampling, contrary to the situation for many prior art solutions.

IV to take a pressurized water sample from the lower end outlet and optional further fluid samples, by opening water sampling valve 20, and taking oil samples by opening oil sampling valve 21 and gas samples by opening gas sampling valve 23, for concentration of dispersed phase analysis.

V then the sample container is depressurized by opening the valve 7 with bleeding action from top of the container, after which fluid phase samples of depressurised fluid are taken, through the same sampling points or successively through the valve 22.

VI to analyze the samples. The pressurized liquid samples have not been subject to dissolved gas flotation, which is crucial for measuring water-in-oil and oil-in-water and liquid-in-gas concentrations correctly before depressurization. Optionally, droplet size distribution of pressurized samples can be undertaken if feasible sensor means, such as a window and an optical dark-field sensor with appropriate software, or an inline analytical instrument, is available on site or is included in the sample container arrangement.

Reference is made to FIG. 2, illustrating an alternative embodiment of a sample container arrangement of the invention. More specifically, the container is not standing but laying. However, it is in principle identical or similar with the embodiment illustrated in FIG. 1, and identical or similar features have the same reference numerical or character, for which reason reference is given to the description of the container of FIG. 1 for a description of the features and function of the container of FIG. 2 also.

The sample container arrangement of the invention can comprise any features as here described or illustrated, in any operative combination, each such operative combination is an embodiment of the sample container arrangement of the invention. The method of the invention can comprise any features or steps as here described or illustrated, in any operative combination, each such operative combination is an embodiment of the method of the invention.

The invention claimed is:

1. A system for collecting multiphase samples of gas and liquid that are representative with respect to oil concentration, oil droplet size and oil droplet size distribution, the system comprising:
a sample container with an upper end, a lower end and a container volume for sample collection;
an inlet connected to the upper end, the inlet being positioned within a gas filled elevation above a liquid level for pressurized sample collection,
a first outlet fluidly coupled to a valve having a bleeding function, the first outlet being positioned in the upper end or part of the container volume so that the first outlet is positioned at a level below or equal to the the inlet; and
a second outlet connected to the lower end of the sample container.

2. The system according to claim 1, wherein the first outlet is disposed at a level corresponding to a maximum filling level of a pressurized liquid, above which maximum filling level is a pressurized gas.

3. The system according to claim 1, comprising:
wherein the first outlet is arranged from the a upper end of the sample container and the second outlet is arranged from the lower end of the sample container; and
wherein the first outlet is positioned within the sample container at an elevation level corresponding to a gas phase and the second outlet is positioned within the sample container at an elevation level corresponding to a water phase.

4. The sample container according to claim 1, wherein outlets (13) are arranged from the side of the container at different elevation levels (11, 10, 12).

5. The system according to claim 1, wherein diameters of tubing associated with the first outlet and the second outlet are smaller than a diameter of an inlet tube that is coupled to the inlet.

6. The system according to claim 1, comprising:
a third outlet positioned within the container volume; and
wherein the second outlet is in fluid communication with a first pressurized liquid phase and the third outlet is in fluid communication with a second pressurized liquid phase.

7. The sample container according to claim 6, comprising:
wherein the first outlet, the second outlet, and the third outlet are arranged from ends of the sample container;
wherein the first outlet is positioned to collect a sample of a gas phase, the second outlet is positioned to collect a sample of a water phase, and the third outlet is positioned to collect an oil phase.

8. The sample container according to claim 6, wherein outlets (13) are arranged from the side of the container at different elevation levels (11, 10, 12).

9. The sample container according to claim 6, wherein a diameter of the first outlet, a diameter of the second outlet, and a diameter of the third outlet is less than a diameter of the inlet.

10. A method for collecting multiphase samples of gas and liquid, such as oil in water samples that are representative with respect to oil concentration, oil droplet size, and oil droplet size distribution, using a sample container, the method comprising the steps of:
opening an inlet valve of a sample container in order to pressurize the sample container to a process pressure, the sample container comprising:
an upper end;
a lower end;
a container volume for sample collection disposed between the upper end and the lower end, the container volume being isobaric for liquid collected during pressurization of the sample container;
an inlet coupled to the inlet valve;
a first outlet coupled to the upper end of the container volume;
a first valve coupled to the first outlet, the first valve comprising a bleeding function;
a second outlet coupled to the lower end of the container volume; and
a second valve coupled to the second outlet;
emptying the container volume by bleeding out liquid from the lower end of the container volume;
closing, after liquid has been emptied from the sample container, the second valve;
opening the first valve to fill up the container volume with liquid up to a liquid filling level that is not higher than the first outlet;
maintaining a gas volume in the upper end of the sample container; and
collecting a first pressurized liquid sample from the second outlet.

11. The method according to claim 10, comprising:
collecting a second pressurized phase sample from the first outlet and a third pressurized phase sample from a third outlet, the third outlet being positioned to collect a sample from the container volume; and
wherein samples from the first outlet, the second outlet, and the third outlet correspond to elevation levels for respective phases of fluid within the sample container;
depressurizing the sample container by bleeding off pressure; and
collecting a depressurized fluid phase sample of fluid.

12. The method according to claim 11, whereby
a. the pressurized phase samples are subject to oil-in-water and water-in-oil concentration measurements;
b. the depressurized samples are subject to oil-in-water and water-in-oil concentration measurements;
c. oil-in-water and water-in-oil droplet size analysis are undertaken on depressurized/affected samples of oil and water, respectively; and
d. a relative difference between a) and b) are used to qualify c) or to quantify real values of c).

* * * * *